(12) United States Patent
Thompson

(10) Patent No.: US 6,511,457 B2
(45) Date of Patent: Jan. 28, 2003

(54) AIRLESS SYRINGE

(76) Inventor: Garey Thompson, P.O. Box 731, Dayton, NJ (US) 08810

( * ) Notice: Subject to any disclaimer, the term of this patent is extended or adjusted under 35 U.S.C. 154(b) by 12 days.

(21) Appl. No.: 09/848,200

(22) Filed: May 4, 2001

(65) Prior Publication Data

US 2002/0165496 A1 Nov. 7, 2002

(51) Int. Cl.$^7$ .................................................. A61M 1/00
(52) U.S. Cl. ........................................ 604/125; 604/122
(58) Field of Search ................................ 604/181, 190, 604/218, 247, 36, 122, 123, 124, 125, 126, 127

(56) References Cited

U.S. PATENT DOCUMENTS

| | | | | |
|---|---|---|---|---|
| 2,263,865 A | * | 11/1941 | Bailen | 604/125 |
| 3,291,128 A | * | 12/1966 | O'Neil | 222/386 |
| 3,809,298 A | * | 5/1974 | Harris et al. | 222/386 |
| 4,318,400 A | * | 3/1982 | Peery et al. | 128/DIG. 12 |
| 5,308,329 A | * | 5/1994 | Mazur et al. | 604/110 |
| 5,385,551 A | * | 1/1995 | Shaw | 604/110 |
| 5,401,246 A | * | 3/1995 | Mazur et al. | 604/110 |
| 5,466,219 A | * | 11/1995 | Lynn et al. | 604/86 |
| 5,531,672 A | * | 7/1996 | Lynn | 600/578 |
| 5,573,515 A | * | 11/1996 | Wilson et al. | 128/DIG. 12 |
| 5,800,397 A | * | 9/1998 | Wilson et al. | 137/625.67 |
| 5,882,343 A | * | 3/1999 | Wilson et al. | 604/152 |
| 6,071,301 A | * | 3/2000 | Cragg et al. | 604/265 |
| 6,063,052 A | * | 5/2000 | Uber, III et al. | 604/154 |
| 6,086,607 A | * | 7/2000 | Cragg et al. | 604/265 |
| 6,099,502 A | * | 8/2000 | Duchon et al. | 128/DIG. 12 |
| RE36,871 E | * | 9/2000 | Epstein et al. | 604/67 |
| 6,183,497 B1 | * | 2/2001 | Sing et al. | 606/213 |
| 6,200,328 B1 | * | 3/2001 | Cragg et al. | 606/213 |
| 6,221,045 B1 | * | 4/2001 | Duchon et al. | 128/DIG. 1 |
| 6,238,374 B1 | * | 5/2001 | Winkler | 604/256 |
| 6,254,569 B1 | * | 7/2001 | O'Donnell et al. | 604/97.03 |
| 6,328,713 B1 | * | 12/2001 | Hollister | 604/192 |
| 6,344,030 B1 | * | 2/2002 | Duchon et al. | 128/DIG. 1 |
| 2001/0021826 A1 | * | 9/2001 | Winkler | 604/191 |
| 2001/0034509 A1 | * | 10/2001 | Cragg et al. | 604/369 |
| 2001/0041913 A1 | * | 11/2001 | Cragg et al. | 606/213 |
| 2002/0052576 A1 | * | 5/2002 | Massengale | 604/164.01 |
| 2002/0068905 A1 | * | 6/2002 | Cowan et al. | 604/181 |

* cited by examiner

Primary Examiner—Ira S. Lazarus
Assistant Examiner—Andrea M. Ragonese
(74) Attorney, Agent, or Firm—Barbara R. Greenberg

(57) ABSTRACT

A syringe having an air release assembly slidingly clamped to a syringe barrel, the air release assembly having a lower portion with a slider valve insert and an upper portion with a rearward facing chamber. The syringe barrel has an opening at the juncture of the barrel and a front wall and the air release assembly upper and lower portions define an opening. Forward movement of the air release assembly closes the barrel opening and prepares the syringe for fluid filling and fluid ejection. Rearward movement of the air release assembly aligns the barrel opening with the air release assembly opening so that slight plunger pressure ejects barrel liquid trapped air bubbles to an outside environment.

3 Claims, 3 Drawing Sheets

AIRLESS SYRINGE

FIELD OF THE INVENTION

This invention relates to syringes and, more particularly, to a syringe where liquid trapped air in a filled syringe can be conveniently and readily expelled and to a method of using such a syringe.

BACKGROUND OF THE INVENTION

One method for separating trapped air from a liquid contained in a filled syringe is described in U.S. Pat. No. 3,809,298. This patent discloses a syringe having a barrel with a bore communicating with a needle bore, the barrel bore having a distal enlarged portion where air trapped in a withdrawn liquid can escape from the liquid and remain in the enlarged portion while liquid is expelled from the syringe. It can be difficult to trap all air bubbles at the same time, especially if the air volume is greater than the enlargement. Also, when the liquid is expelled, no barrier prevents the air from returning to the liquid.

In U.S. Pat. No. 3,291,128, a hypodermic syringe is constructed with a barrel and annular ribs extending about a piston. The annular ribs must be elastic in order to provide for expulsion of trapped air from the barrel. However, if the ribs do not reform and immediately establish a sealing engagement with the barrel wall, leakage or discharge of syringe liquid can result.

In U.S. Pat. No. 2,263,865, either a spring operated knob or a sleeve cover are retracted to open an air hold and release liquid trapped air bubbles. When the knob or sleeve are released to allow air rejection, fluid can also be released to the outside of a syringe with messy and sometimes dangerous results. In addition, a sleeve cover can obliterate volume markings on a syringe. The present invention addresses the problems cited in prior art inventions by providing a reliable and simple means for air bubble release from liquids contained in syringes.

A primary objective of the present invention is to provide a sliding chamber means for removal of trapped air bubbles from syringe delivered liquids where a simple positive movement of the syringe plunger reliably releases small and large volumes of air without liquid spill.

Another objective of the invention is to provide a syringe where the user does not have to continuously tap the syringe and move a plunger back and forth to remove trapped air.

Still another objective is to provide a means for delivering an accurate volume of liquid to a user via syringe injection.

Finally, an objective of the present invention is to provide a sanitary and efficient means for syringe liquid trapped gas removal when a user has painful and/or weak fingers and is not able to vigorously snap or manipulate a syringe in order to remove gas bubbles.

SUMMARY OF THE INVENTION

The present invention provides an airless syringe with means for efficiently removing liquid trapped air bubbles so that accurate liquid volume measurements are possible comprising a cylindrical barrel with a sealed forward wall, the barrel defining a small opening at the barrel's juncture with the sealed wall. The sealed wall exterior is provided with a centrally located tapered shank portion adapted to receive a conventional hypodermic needle inserted so as to be in communication with the barrel interior. The needle and the needle insertion means have no patentable significance relative to the invention herein. Within the barrel resides a plunger carrying a forward end piston. In order to provide a snug fit between the piston and barrel interior wall, the piston diameter is substantially equal in size to the barrel wall inside diameter. A positive movement of the plunger slides the piston smoothly back and forth inside the barrel.

An air release assembly located above the small barrel opening adjacent to the syringe front wall is slidingly mounted to the barrel exterior surface. The air release assembly is comprised of a barrel adjacent portion with means for smooth sliding on the barrel exterior surface and an upper chamber portion where trapped air is expelled. An opening extends through the sliding means portion and chamber portion for air transport from the barrel interior to an exterior environment. A mounting clamp slidingly clasps the air release assembly to the syringe barrel.

The airless syringe is filled with liquid when a user slides the air release assembly forward to a closed position, places the hollow needle below a liquid surface and pulls the plunger back to draw liquid into the syringe. Often air bubbles enter with the liquid. The airless syringe is titled so the needle is positioned upward causing trapped air to move to the area of the barrel opening. Now the user slides the air release assembly backward to an open position where the air release assembly opening is aligned with the barrel opening. Forward movement of the plunger pushes syringe trapped air through the barrel opening and the air release assembly opening into the upper portion chamber where trapped air is expelled. An absorbent material designed to receive syringe fluid accompanying expelled air resides in the chamber. Next, a simple forward movement of the air release assembly to a closed position prepares the syringe for use. By positive movement of the plunger, a user can safely inject a measured amount of liquid free of air bubbles.

The above prominent advantages and features of the present invention are further and more fully described by the following description which makes reference to the attached drawings.

DETAILED DESCRIPTION OF THE INVENTION

Figure 1:
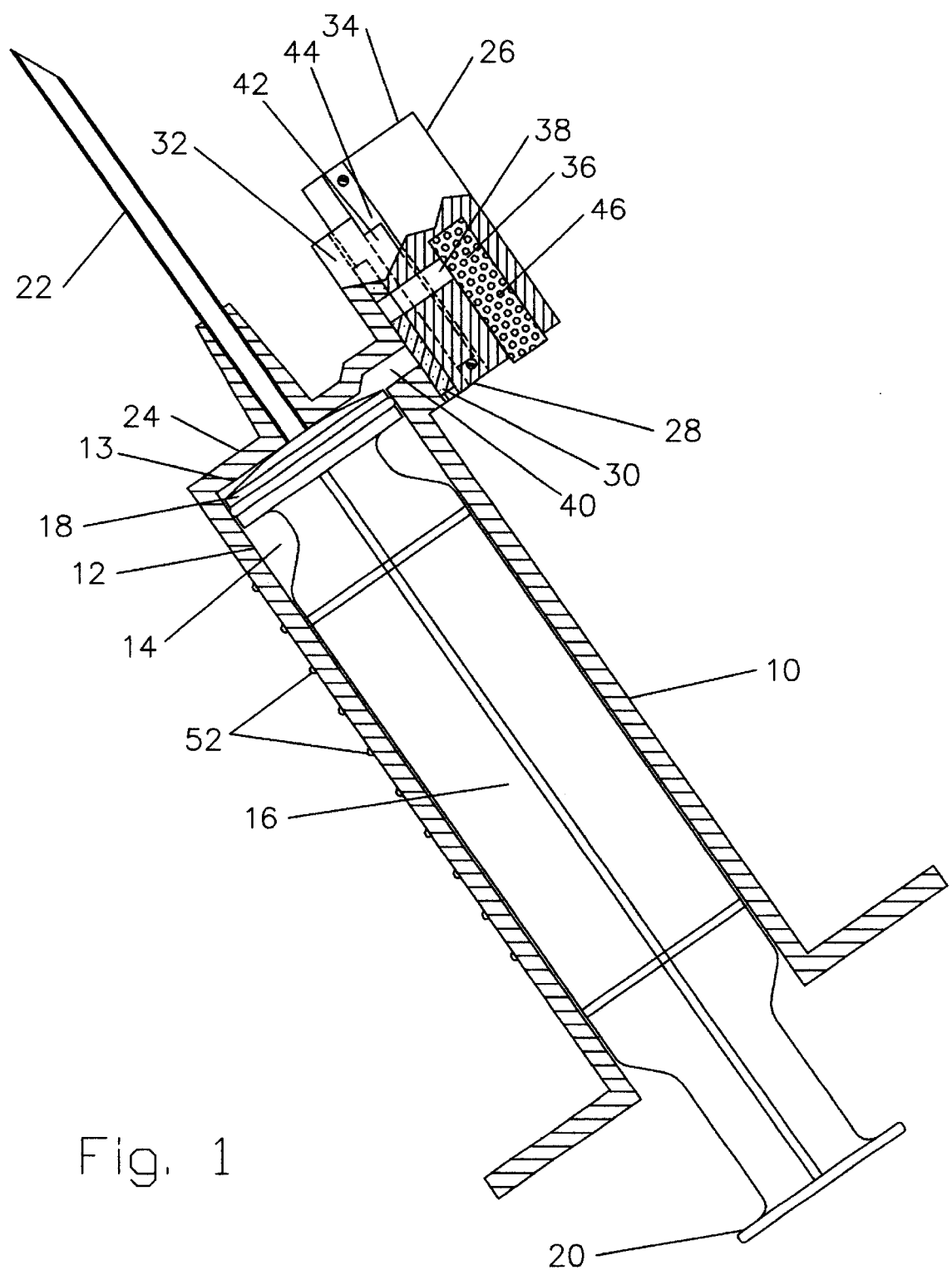
FIG. 1 is a partial section of the airless syringe showing the air release assembly opening unaligned with the syringe barrel opening depicting barrel filling and barrel liquid ejection positions.

Referring now to the drawings, in FIG. 1 an airless syringe 10 is shown having a cylindrical barrel 12 with a front wall 13, the barrel 12 and wall 13 defining a fluid chamber 14 and a slidingly fitted plunger 16 provided with a forward end piston 18 and rearward end thumb button 20. A hollow needle 22 mounted on the exterior surface 24 of the barrel front wall 13 is in open communication with the fluid chamber 14.

Figure 2:
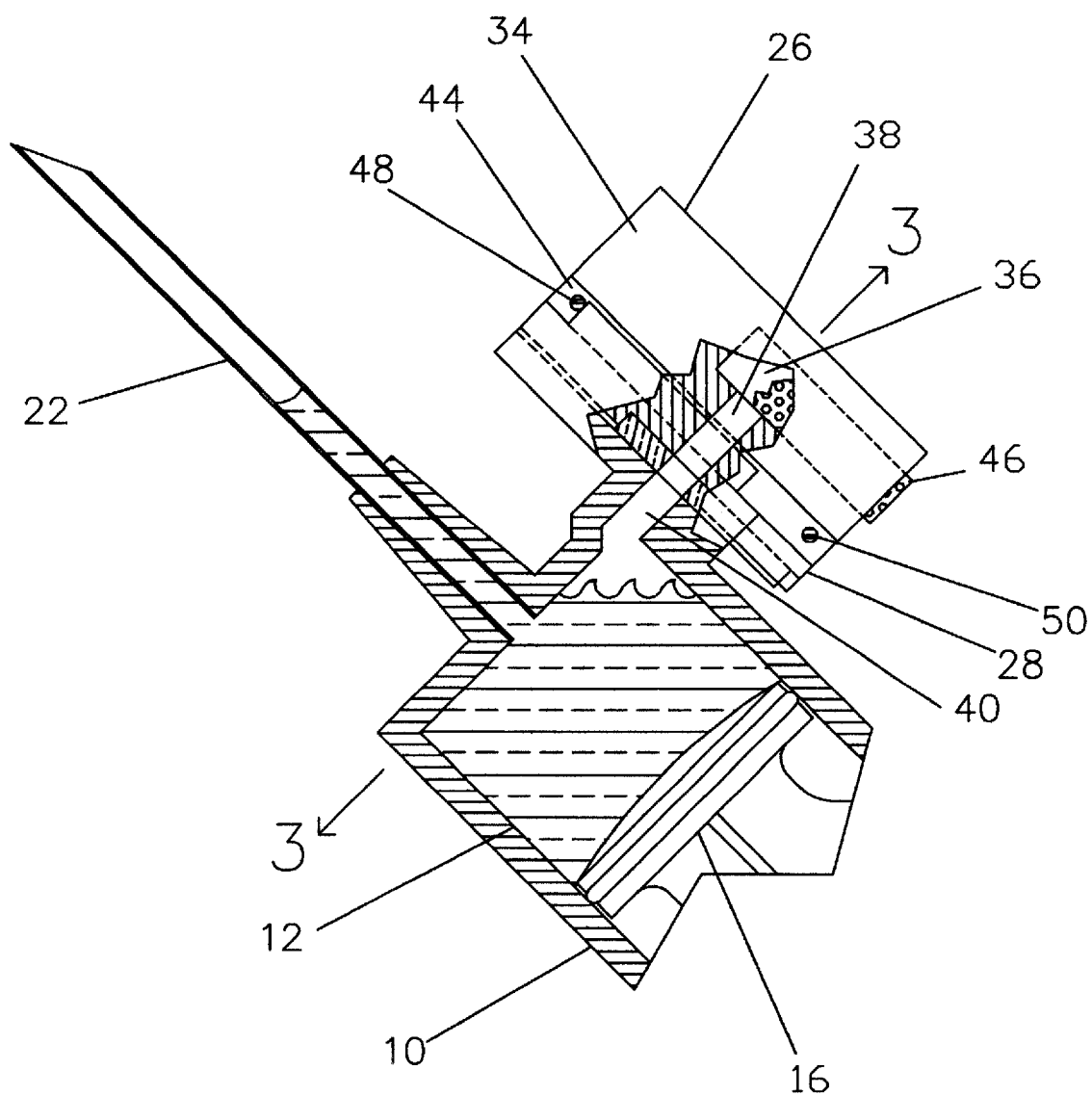
FIG. 2 is a partial section of the airless syringe showing the air release chamber opening aligned with the syringe barrel opening ready for air bubble ejection.

An air release assembly 26 comprising a lower portion 28 having a slider valve insert 30 placed within the lower portion 28 surface adjacent to the barrel 12 surface and barrel extension 32 surface and an upper portion 34 having a chamber 36, the chamber 36 opening rearward to face the plunger 16 thumb button 20. The air release assembly 26 lower portion 28 and upper portion 34 define an opening 38 that extends through the slider valve insert 30 to terminate in chamber 36. A barrel 12 opening 40 at the junction of the barrel 12 and front wall 13 can be aligned with opening 38 by sliding the air release assembly 26 rearward so that the opening 38 is directly over barrel 12 opening 40 as shown in FIG. 2. A clamp 42 slidingly engages the air release assembly 26 via a track 44 allowing easy sliding of air release assembly 26 in order to open and close barrel 12 opening 40. Clamp 42 is mounted on a barrel 12 extension 32 located forward of opening 40.

In FIG. 1, barrel 12 opening 40 is in a closed position indicating readiness for syringe 10 filling. To accomplish this, hollow needle 22 is immersed in a liquid (not shown) and plunger 16 is slowly retracted until a desired volume of liquid fills fluid chamber 14. In a preferred embodiment, calibrated markings on barrel 12 opposite the air release assembly 26 indicate fluid volume. However, often liquid trapped air bubbles prevent accurate volume measurement. In the airless syringe 10, air bubble release proceeds in the following manner.

Referring to FIG. 2, the airless syringe 10 is ready for air bubble ejection. Tipping syringe 10 so that the hollow needle 22 is higher than the barrel 12, preferably at a 45° angle, with the air release assembly 26 facing upward, trapped air bubbles readily move to the barrel opening 40. Next, the air release assembly 26 is slidingly moved rearward to align barrel opening 40 with air release assembly opening 38. A quick, snapping rearward moving motion starts air travel through barrel opening 40. Next, plunger 16 is very slowly pushed forward until trapped air bubbles are ejected through openings 38, 40 and liquid is observed to enter chamber 36. An absorbent material 46, preferably cotton, placed in chamber 36 absorbs excess liquid. In addition to cotton, sponge or sponge like material or any absorbent open cell material can be used. The absorbent material can fill the chamber 36 if the material has air release capacity. Immediately after liquid is observed in chamber 36, the air release assembly 26 is slidingly pushed forward to close barrel opening 40 and airless syringe 10 is ready for liquid injection by way of the hollow needle 22. To control the air release assembly 26 sliding movements, track 44 located between the lower portion 28 and upper portion 34 is provided with a front stop 48 and a back stop 50 delineating maximum forward and rearward air release assembly 26 positions. Preferably, the stops, 48, 50 are thin metal rods. However, stops 48, 50 can be molded from the same material used for air release assembly 26 construction such as a plastic material. To properly close barrel 12 opening 40 after air bubble release, the air release assembly 26 should slide completely forward and to achieve accurate opening 40 and opening 38 alignment, the air release assembly 26 should slide completely rearward.

Figure 3:
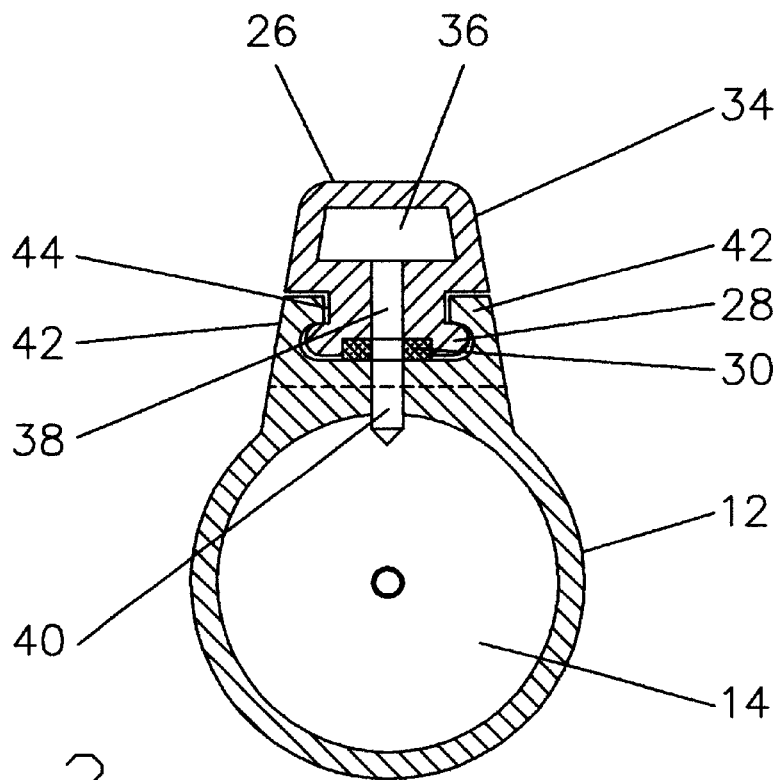
FIG. 3 is a cross sectional view taken along line 3—3 of FIG. 2.
Figure 4:
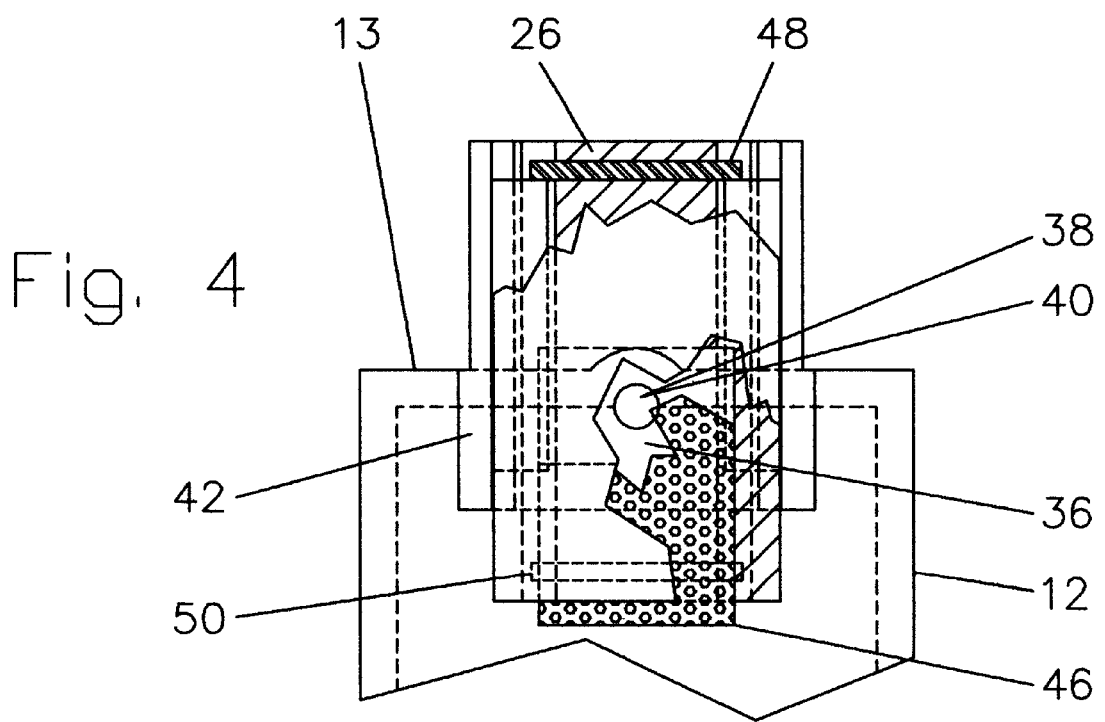
FIG. 4 is a partial section top view of the air release assembly ready for air bubble ejection.

Referring to FIG. 3, a cross sectional view taken along line 3—3 of FIG. 2, the pathway for air bubble release from the fluid chamber 14 is traced. Barrel 12 opening 40 is aligned with air release assembly 26 opening 38 that opens into chamber 36 where air is ejected and liquid is absorbed. In FIG. 4, looking down from chamber 36, the aligned openings 38, 40 at the point of front wall 13 juncture with barrel 12, are aligned for air bubble ejection.

Because of the placement and construction of the air release assembly 26, an airless syringe 10 user can remove liquid trapped air with one hand and little effort. This benefits an individual who has weak and/or painful hands. Graduated volume markings 52, in a preferred embodiment, are opposite the air release assembly 26 but can be placed on any clearly observable barrel 12 position.

The airless syringe 10 barrel 12 is composed of a transparent glass or plastic material. The plunger 16 can be constructed from a rigid material such as a thermosetting plastic and piston 18, at its contact point with the barrel 12 interior surface, can be made of a tough resilient material in order to fit tightly but travel slidingly within barrel 12. The air release assembly 26 slider valve insert 30 should also be constructed of a resilient material, preferably black rubber for easy sliding and tight sealing of barrel opening 40. It should be noted that the airless syringe 10 can be used to eject any liquid trapped gas present in the barrel 12 fluid chamber 14.

With regard to the above description, it will be apparent to those skilled in the art, that the present invention is susceptible to many different embodiments without departing from the spirit and scope of the invention. Therefore, it is not intended that the present invention be unduly limited by the foregoing drawings and description.

What is claimed is:

1. A syringe with air removal capability comprising
    a barrel having a front wall with an opening at said barrel and front wall juncture;
    a barrel extension located forward of said opening;
    a fluid chamber defined by said barrel and said front wall;
    a slidingly fitted plunger mounted within said barrel fluid chamber;
    a hollow needle in open communication with said fluid chamber; and
    an air release assembly, said air release assembly having a lower portion containing a slider valve insert adjacent to a barrel surface and adjacent to a barrel extension surface and an upper portion having a rearward opening chamber, said upper portion and said lower portion defining an opening beginning at said slider valve insert and terminating in said upper portion chamber, said opening alignable with said barrel and front wall juncture opening and said air release assembly slidingly engaged by a clamp, said clamp residing on a track, said track terminating with front and rear stops.

2. The syringe of claim 1 wherein said upper portion chamber contains an absorbent material.

3. The syringe of claim 1 wherein said barrel surface has graduated volume markings.

* * * * *